(12) United States Patent  
Boitano (10) Patent No.: US 8,599,215 B1
(45) Date of Patent: Dec. 3, 2013

(54) METHOD, APPARATUS AND SYSTEM FOR JOINING IMAGE VOLUME DATA

(75) Inventor: Michael Boitano, Smithtown, NY (US)

(73) Assignee: Fonar Corporation, Melville, NY (US)

( * ) Notice: Subject to any disclaimer, the term of this patent is extended or adjusted under 35 U.S.C. 154(b) by 799 days.

(21) Appl. No.: 12/387,823

(22) Filed: May 7, 2009

Related U.S. Application Data

(60) Provisional application No. 61/126,752, filed on May 7, 2008.

(51) Int. Cl.
*G06T 11/60* (2006.01)
*G09G 5/00* (2006.01)

(52) U.S. Cl.
USPC ........... 345/629; 345/419; 345/422; 345/630; 345/631; 345/632; 345/633; 345/634; 382/131

(58) Field of Classification Search
USPC .................... 345/419, 422, 629–634; 382/131
See application file for complete search history.

(56) References Cited

U.S. PATENT DOCUMENTS

| | | | |
|---|---|---|---|
| 3,810,254 A | 5/1974 | Utsumi et al. |
| 4,407,292 A | 10/1983 | Edrich et al. |
| 4,411,270 A | 10/1983 | Damadian |
| 4,534,076 A | 8/1985 | Barge |
| 4,534,358 A | 8/1985 | Young |
| D283,858 S | 5/1986 | Opsvik |
| 4,608,991 A | 9/1986 | Rollwitz |
| 4,613,820 A | 9/1986 | Edelstein et al. |
| 4,614,378 A | 9/1986 | Picou |
| 4,641,119 A | 2/1987 | Moore |
| 4,651,099 A | 3/1987 | Vinegar et al. |
| 4,663,592 A | 5/1987 | Yamaguchi et al. |
| 4,664,275 A | 5/1987 | Kasai et al. |
| 4,668,915 A | 5/1987 | Daubin et al. |
| 4,672,346 A | 6/1987 | Miyamoto et al. |
| 4,675,609 A | 6/1987 | Danby et al. |
| 4,707,663 A | 11/1987 | Minkoff et al. |
| 4,766,378 A | 8/1988 | Danby et al. |
| 4,767,160 A | 8/1988 | Mengshoel et al. |
| 4,770,182 A | 9/1988 | Damadian et al. |
| 4,777,464 A | 10/1988 | Takabatashi et al. |
| 4,816,765 A | 3/1989 | Boskamp et al. |
| 4,829,252 A | 5/1989 | Kaufman |
| 4,875,485 A | 10/1989 | Matsutani |
| 4,908,844 A | 3/1990 | Hasegawa et al. |
| 4,920,318 A | 4/1990 | Misic et al. |
| 4,924,198 A | 5/1990 | Laskaris |
| 4,943,774 A | 7/1990 | Breneman et al. |
| 4,985,678 A | 1/1991 | Gangarosa et al. |
| 5,008,624 A | 4/1991 | Yoshida et al. |
| 5,030,915 A | 7/1991 | Boskamp et al. |
| 5,050,605 A | 9/1991 | Eydelman et al. |
| 5,061,897 A | 10/1991 | Danby et al. |
| 5,065,701 A | 11/1991 | Punt |
| 5,065,761 A | 11/1991 | Pell |

(Continued)

*Primary Examiner* — Xiao M. Wu
*Assistant Examiner* — Todd Buttram
(74) *Attorney, Agent, or Firm* — Lerner, David, Littenberg, Krumholz & Mentlik, LLP (57) ABSTRACT

An apparatus and method for joining two MRI image data sets to form a composite image. The images are joined together at one or more places along the common area by processing the first and second image data using the square of the normalized intensity difference between at least one group of pixels in the first image data and another group of pixels in the second image data.

13 Claims, 9 Drawing Sheets

(56) References Cited

U.S. PATENT DOCUMENTS

| | | | |
|---|---|---|---|
| 5,081,665 | A | 1/1992 | Kostich |
| 5,124,651 | A | 6/1992 | Danby et al. |
| 5,134,374 | A | 7/1992 | Breneman et al. |
| 5,153,517 | A | 10/1992 | Oppelt et al. |
| 5,153,546 | A | 10/1992 | Laskaris |
| 5,155,758 | A | 10/1992 | Vogl |
| 5,162,768 | A | 11/1992 | McDougall et al. |
| 5,171,296 | A | 12/1992 | Herman |
| 5,194,810 | A | 3/1993 | Breneman et al. |
| 5,197,474 | A | 3/1993 | Englund et al. |
| 5,207,224 | A | 5/1993 | Dickinson et al. |
| 5,221,165 | A | 6/1993 | Goszczynski |
| 5,229,723 | A | 7/1993 | Sakurai et al. |
| 5,250,901 | A | 10/1993 | Kaufman et al. |
| 5,251,961 | A | 10/1993 | Pass |
| 5,256,971 | A | 10/1993 | Boskamp |
| 5,274,332 | A | 12/1993 | Jaskolski et al. |
| 5,291,890 | A | 3/1994 | Cline et al. |
| 5,304,932 | A | 4/1994 | Carlson |
| 5,305,365 | A | 4/1994 | Coe |
| 5,305,749 | A | 4/1994 | Li et al. |
| 5,315,244 | A | 5/1994 | Griebeler |
| 5,315,276 | A | 5/1994 | Huson et al. |
| 5,317,297 | A | 5/1994 | Kaufman et al. |
| 5,323,113 | A | 6/1994 | Cory et al. |
| 5,349,956 | A | 9/1994 | Bonutti |
| 5,382,904 | A | 1/1995 | Pissanetzky |
| 5,382,905 | A | 1/1995 | Miyata et al. |
| 5,386,447 | A | 1/1995 | Siczek |
| 5,394,087 | A | 2/1995 | Molyneaux |
| 5,412,363 | A | 5/1995 | Breneman et al. |
| 5,471,142 | A | 11/1995 | Wang et al. |
| 5,473,251 | A | 12/1995 | Mori |
| 5,475,885 | A | 12/1995 | Ishikawa et al. |
| 5,477,146 | A | 12/1995 | Jones |
| 5,490,513 | A | 2/1996 | Damadian et al. |
| 5,515,863 | A | 5/1996 | Damadian |
| 5,519,372 | A | 5/1996 | Palkovich et al. |
| 5,548,218 | A | 8/1996 | Lu |
| 5,553,777 | A | 9/1996 | Lampe |
| 5,566,681 | A | 10/1996 | Manwaring et al. |
| 5,592,090 | A | 1/1997 | Pissanetzky |
| 5,606,970 | A | 3/1997 | Damadian |
| 5,621,323 | A | 4/1997 | Larsen |
| 5,623,241 | A | 4/1997 | Minkoff |
| 5,640,958 | A | 6/1997 | Bonutti |
| 5,652,517 | A | 7/1997 | Maki et al. |
| 5,654,603 | A | 8/1997 | Sung et al. |
| 5,666,056 | A | 9/1997 | Cuppen et al. |
| 5,671,526 | A | 9/1997 | Merlano et al. |
| 5,680,861 | A | 10/1997 | Rohling |
| 5,682,098 | A | 10/1997 | Vij |
| 5,743,264 | A | 4/1998 | Bonutti |
| 5,754,085 | A | 5/1998 | Danby et al. |
| 5,779,637 | A | 7/1998 | Palkovich et al. |
| 5,836,878 | A | 11/1998 | Mock et al. |
| 5,862,579 | A | 1/1999 | Blumberg et al. |
| 5,929,639 | A | 7/1999 | Doty |
| 5,951,474 | A | 9/1999 | Matsunaga et al. |
| D417,085 | S | 11/1999 | Kanwetz, II |
| 5,983,424 | A | 11/1999 | Naslund et al. |
| 5,988,173 | A | 11/1999 | Scruggs |
| 6,008,649 | A | 12/1999 | Boskamp et al. |
| 6,014,070 | A | 1/2000 | Danby et al. |
| 6,023,165 | A | 2/2000 | Damadian et al. |
| 6,075,364 | A | 6/2000 | Damadian et al. |
| 6,122,541 | A | 9/2000 | Cosman et al. |
| 6,137,291 | A | 10/2000 | Szumowski et al. |
| 6,138,302 | A | 10/2000 | Sashin et al. |
| 6,144,204 | A | 11/2000 | Sementchenko |
| 6,150,819 | A | 11/2000 | Laskaris et al. |
| 6,150,820 | A | 11/2000 | Damadian et al. |
| 6,201,394 | B1 | 3/2001 | Danby et al. |
| 6,208,144 | B1 | 3/2001 | McGinley et al. |
| 6,226,856 | B1 | 5/2001 | Kazama et al. |
| 6,246,900 | B1 | 6/2001 | Cosman et al. |
| 6,249,121 | B1 | 6/2001 | Boskamp et al. |
| 6,249,695 | B1 | 6/2001 | Damadian |
| 6,285,188 | B1 | 9/2001 | Sakakura et al. |
| 6,332,034 | B1* | 12/2001 | Makram-Ebeid et al. .... 382/128 |
| 6,357,066 | B1 | 3/2002 | Pierce |
| 6,369,571 | B1 | 4/2002 | Damadian et al. |
| 6,377,044 | B1 | 4/2002 | Burl et al. |
| 6,385,481 | B2 | 5/2002 | Nose et al. |
| 6,411,088 | B1 | 6/2002 | Kuth et al. |
| 6,414,490 | B1 | 7/2002 | Damadian et al. |
| 6,424,854 | B2 | 7/2002 | Hayashi et al. |
| 6,456,075 | B1 | 9/2002 | Damadian et al. |
| 6,468,218 | B1* | 10/2002 | Chen et al. .................. 600/443 |
| 6,504,371 | B1 | 1/2003 | Damadian et al. |
| 6,591,128 | B1 | 7/2003 | Wu et al. |
| 6,677,753 | B1 | 1/2004 | Danby et al. |
| 6,792,257 | B2 | 9/2004 | Rabe et al. |
| 6,806,711 | B2 | 10/2004 | Reykowski |
| 6,828,792 | B1 | 12/2004 | Danby et al. |
| 6,850,064 | B1 | 2/2005 | Srinivasan |
| 6,882,149 | B2 | 4/2005 | Nitz et al. |
| 6,882,877 | B2 | 4/2005 | Bonutti |
| 6,894,495 | B2 | 5/2005 | Kan |
| 7,049,819 | B2 | 5/2006 | Chan et al. |
| 7,221,161 | B2 | 5/2007 | Fujita et al. |
| 7,245,127 | B2 | 7/2007 | Feng et al. |
| 7,348,778 | B2 | 3/2008 | Chu et al. |
| 7,474,098 | B2 | 1/2009 | King |
| 2003/0156758 | A1* | 8/2003 | Bromiley et al. .............. 382/219 |
| 2004/0204644 | A1* | 10/2004 | Tsougarakis et al. ......... 600/410 |
| 2005/0122343 | A1* | 6/2005 | Bailey et al. .................. 345/619 |
| 2005/0213849 | A1* | 9/2005 | Kreang-Arekul et al. .... 382/284 |
| 2007/0092121 | A1* | 4/2007 | Periaswamy et al. ......... 382/128 |
| 2007/0165921 | A1* | 7/2007 | Agam et al. .................. 382/128 |
| 2008/0292194 | A1* | 11/2008 | Schmidt et al. ............... 382/217 |
| 2008/0317317 | A1* | 12/2008 | Shekhar et al. ............... 382/131 |
| 2010/0111375 | A1* | 5/2010 | Jones ............................ 382/118 |

* cited by examiner

METHOD, APPARATUS AND SYSTEM FOR JOINING IMAGE VOLUME DATA

CROSS-REFERENCE TO RELATED APPLICATIONS

This application claims the benefit of the filing date of U.S. Provisional Application No. 61/126,752, filed May 7, 2008, the disclosure of which is hereby incorporated herein by reference.

BACKGROUND

It is sometimes necessary to join together two images to make a larger, composite image. These images typically have some overlapping features in common which must be aligned properly to create the larger image. Typically, in plane translational offsets must be calculated to align the images. The problem is compounded when dealing with 3D volume data. For example, to diagnose and analyze scoliosis using MRI, separate 3D volume data sets of the upper and lower spine are acquired in order to achieve the necessary field-of-view while preserving necessary image quality and detail. In this case, both in-plane and out-of-plane translational offsets must be computed to align the volume data.

Presently used techniques register two images from differing modalities (e.g., MRI and CT) for the purpose of fusing the data. Both modalities cover the same volume of anatomy and several control points are used to identify common features. Having to use two different modalities with several control points increases the complexity of these techniques.

Of utility then are methods and system that reduce the complexity of prior art systems and processes in joining volume image data from a single modality.

SUMMARY

In one aspect, the present invention provides one or more processes and a user interface that allows for 3D alignment of volume image data. This aspect of the invention is used to join together images from the same modality for the purpose of generating a composite image with a larger field-of-view but with the resolution and quality of individual scans.

In another aspect, the present invention preferably requires only one control point placed on a single image from each data set. Given this single data point, 3D volume data is combined to form a larger 3D volume. For example, where one set of image data is displayed on screen and shows a common area of anatomy with a second set of image data, a control point within the common area is selected. Once that selection is made, a search is done through the volumetric overlapping areas. The two image data sets are joined based on minimization of an error function generated from the area surrounding the control point in both volumetric data sets. The area surrounding the control point is referred to as the control point's neighborhood. The neighborhood can be in-plane (two dimensional) or it can include neighboring slices (three dimensional). In the case of two dimensions it may be rectangular and in the case of three dimensions it may be a rectangular prism (rectangular parallelepiped). The size of the neighborhood is chosen to encompass distinguishing features in the images. In the case of MRI spinal images the neighborhood is chosen to be slightly larger than the dimensions of lumbar vertebrae and adjacent discs. The similarity of the pixel intensities of the neighborhoods of an upper control point and a lower control point is determined by computing the error function. The two neighborhoods are then offset from each other in two (or three) dimensions and the error function is re-computed. This process is continued for other offsets, the limits of which are predetermined. Those offsets that produce the minimum error function are chosen as the best overlapping match and the two image volumes are joined using them.

In other embodiments, more than one data point may be used to form a larger 3D volume. More specifically, two 3D volume data sets may be combined into one larger volume, e.g., in the case of MRI diagnosis and analysis of scoliosis, 3D image data of the upper and lower spine are acquired. These two image sets are loaded into the "joining" software program. The center slice of each set is displayed where the images may be adjusted in brightness and contrast using controls provided through a computer interface, e.g., a mouse, stylus, touch screen, etc. If these images are not desired, other images may be selected by computer control, e.g., scroll bars, either in-synch or independently. The images are displayed above and below each other vertically. If their order is incorrect, they may be swapped.

In another aspect of the present invention an apparatus is provided. The apparatus comprises a memory containing executable instructions; and a processor. The processor is preferably programmed using the instructions to receive pixel data associated with a first magnetic resonance image; receive pixel data associated with a second magnetic resonance image; and detect a common area between the first and second images. Further in accordance with this aspect of the present invention, the processor is also programmed to combine the images together at one or more places along the common area by processing the first and second image data using the square of the normalized intensity difference between at least one group of pixels in the first image data and another group of pixels in the second image data and display the combined image.

Further still in accordance with this aspect of the present invention, the processor is further programmed to display data indicating the offset between the first and second magnetic resonance images in forming the combined image. In addition, in detecting the common area the processor is programmed to search volumetric data associated with the first and second magnetic resonance images based on one or more control points selected in the range.

Further in accordance with this aspect of the present invention, the processor is further programmed to display at least two views of the combined image with one view being orthogonal to the other.

Further still in accordance with this aspect of the present invention, the processor combines the images based on in-plane and out-of-plane offsets.

DESCRIPTION

Figure 1A:
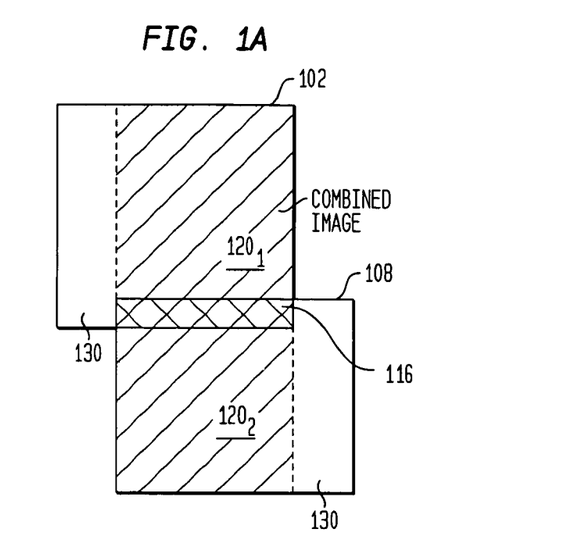
FIG. 1A illustratively depicts in-plane translations of image data of two images in accordance with an aspect of the present invention.
Figure 1B:
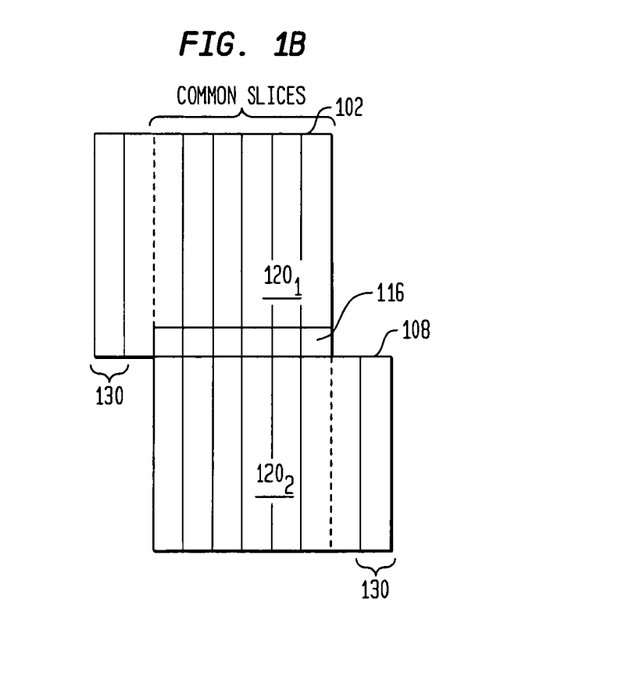
FIG. 1B illustratively depicts out-of-plane translations of image data of two images in accordance with an aspect of the present invention.

Turning now to FIGS. 1A and 1B, there is illustrated two images, top image 102 and bottom image 108, that are taken of portions of a patient's anatomy in accordance with an aspect of the present invention. In the preferred embodiment, the images are taken using the same modality, and most preferably using an MRI system such as that described in commonly assigned U.S. Pat. No. 6,828,792, the disclosure of which is incorporated herein by reference. In addition, though the images shown in the accompanying drawings show the use of the methods and systems in detecting images of the spine, the present invention is not limited to processing only spinal images. The present invention may be applied to making composite images from any portion of a patient's anatomy, including, for example, any organ in the patient's torso.

More specifically, FIG. 1A shows in-plane translations of two images that may be joined or stitched together to form a larger composite image having a desired resolution. As this figure shows, a top image 102 and a bottom image 108 includes common or overlapping data 116, e.g., pixel data, that may be used to form or stitch together the two images. (In FIG. 1A, overlapping data 116 is shown as the cross hatched region.) In addition to overlapping data, both images include non-overlapping data $120_1$, $120_2$ that is used to form the combined image. Some of the non-overlapping data 130 is preferably discarded since it is outside the area of interest.

FIG. 1B shows the out of plane translation and how the discarded and retained image data are processed along this plane. For example, assuming FIG. 1A shows the image data along an x-y plane, FIG. 1B shows the same data along a third dimension, e.g., the z-axis. As is known in the art, MRI accumulates volumetric pixel data in slices. These slices when combined provide the three dimensional images that make this modality popular for looking at the human anatomy since soft tissue and non-soft tissue can be shown in proper anatomical position.

Figure 2A:
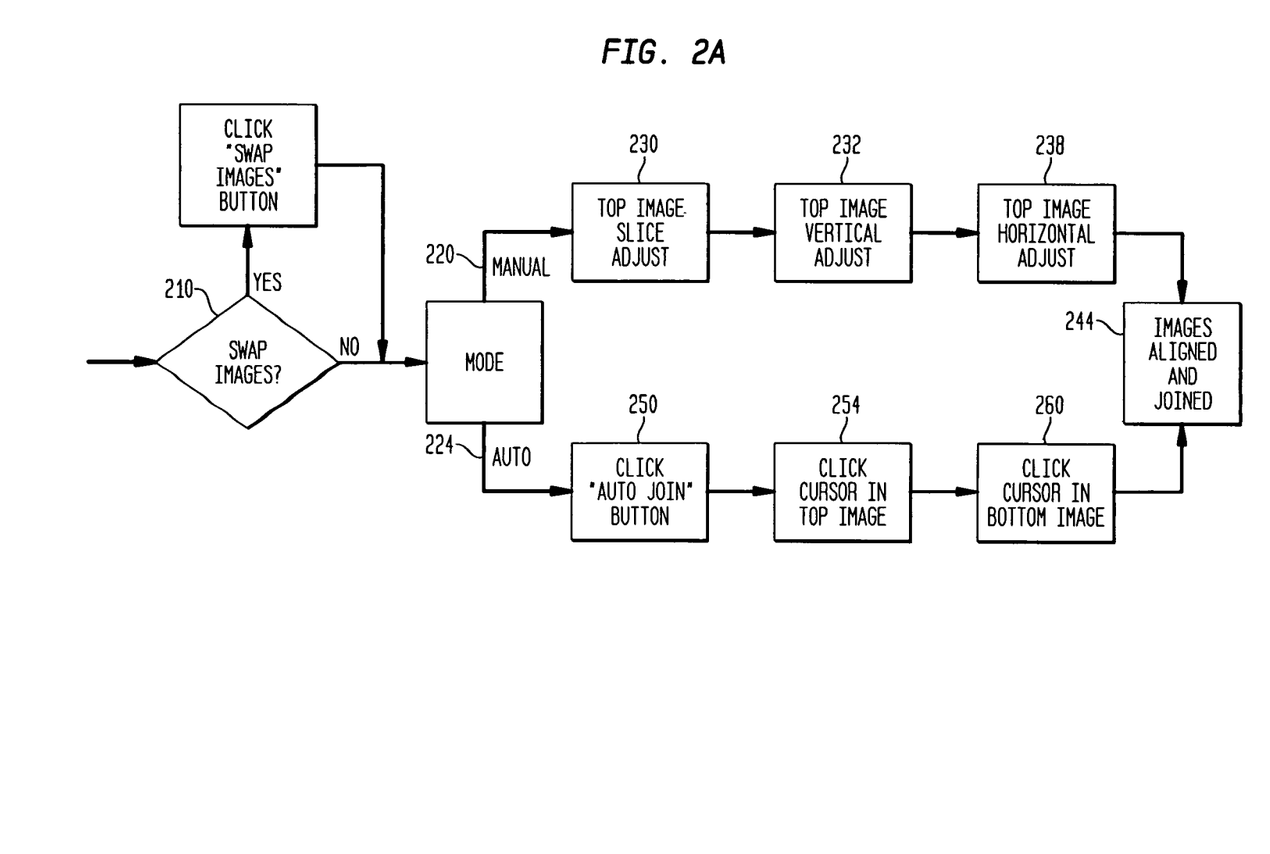
FIG. 2A is a flow chart illustrating a process for joining two image data sets in accordance with an aspect of the present invention.
Figure 2B:
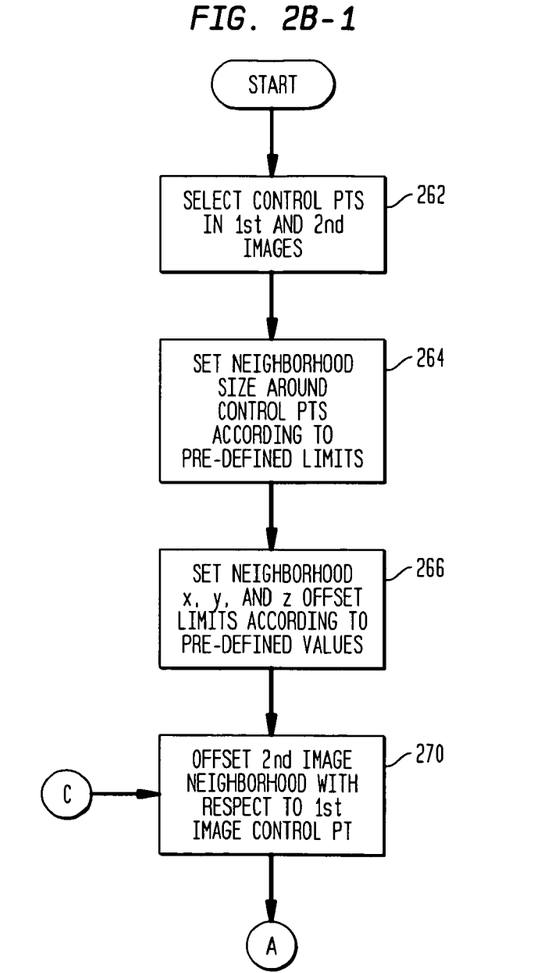
FIG. 2B is a flow chart illustrating a process for joining two image data sets in accordance with an aspect of the present invention.
Figure 2B:
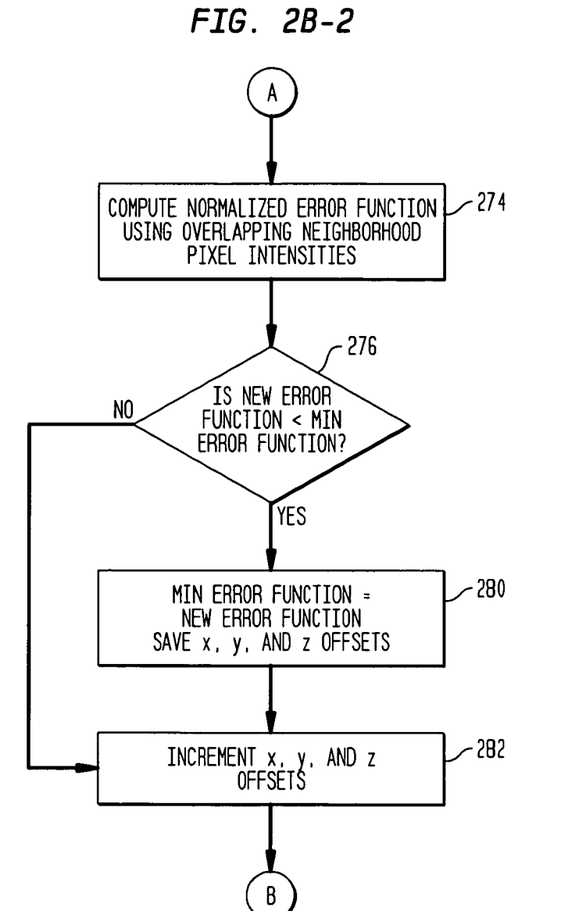
Figure 2B:
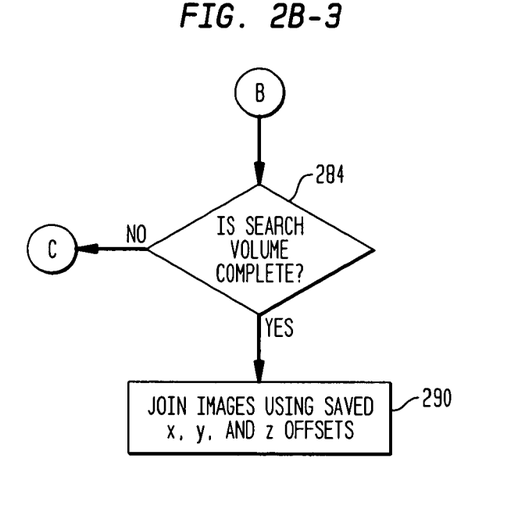
Figure 3A:
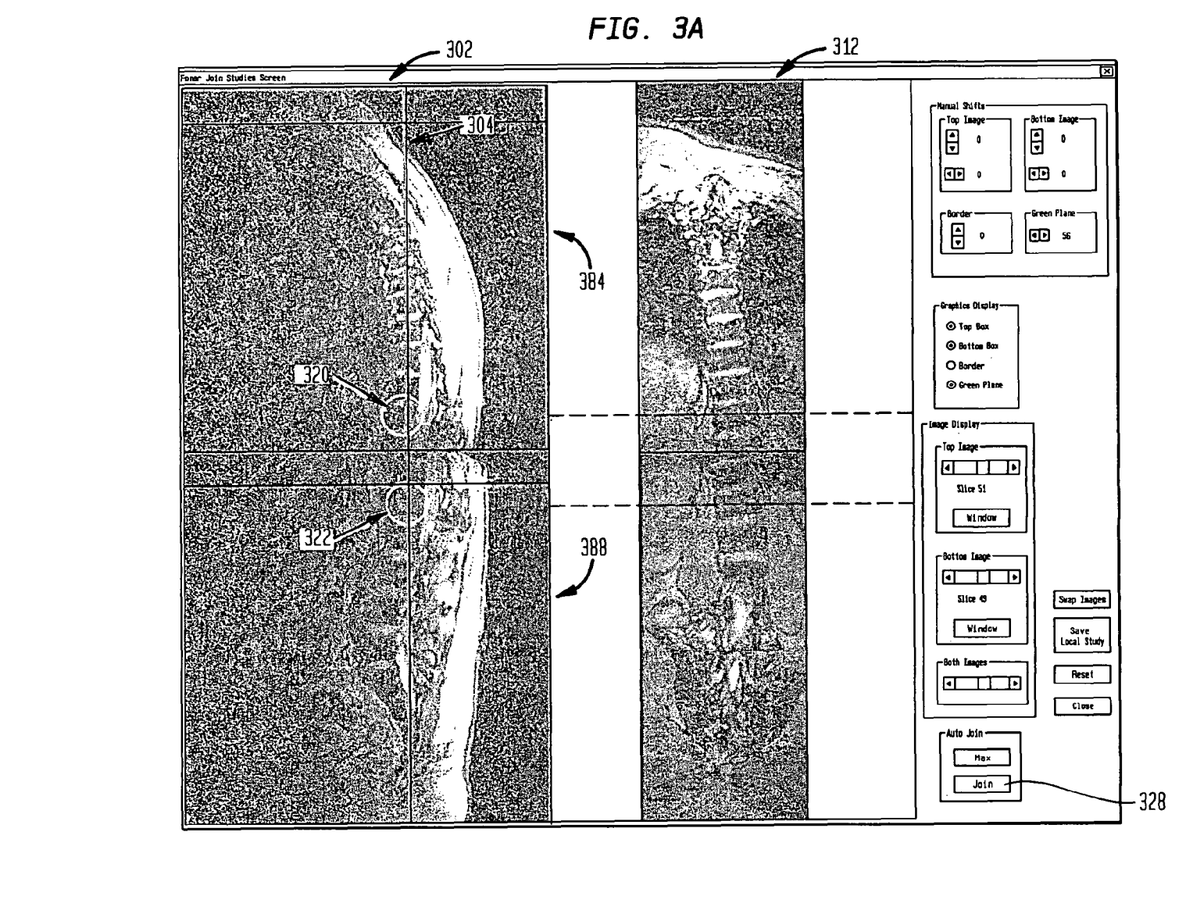
FIGS. 3A and 3B depict a display screen of two images joined in accordance with an aspect of the present invention.
Figure 3B:
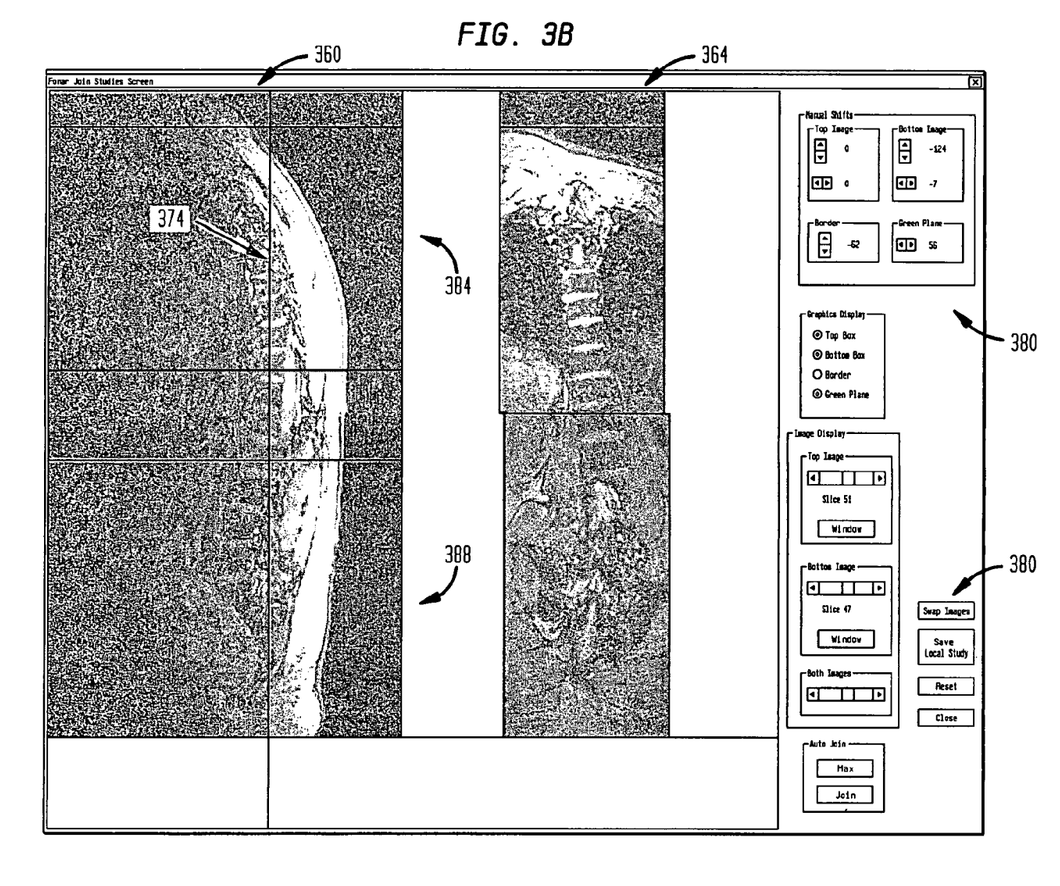

FIG. 2A is a high level flow chart showing a method in accordance with an aspect of the present invention. Preferably two modes of operations are provided: (1) manual mode; and (2) automatic mode. In the manual mode of operation the images may be translated vertically and horizontally relative to each other under computer control until they are aligned properly. For example, tracking balls or other computer input control means may be used to provide the relative movement needed for alignment. FIGS. 3A and 3B show, for example, the use of "Manual Shifts" that may be used to offset the different images relative to each other. By aligning a single image pair, the entire image volume is aligned using the same translational offsets. Out-of-plane alignment may be accomplished similarly by offsetting displayed images or slices. Any data with horizontal coordinates not common to both data sets is not included in the joined data as is shown in FIGS. 1A and 1B.

As shown in FIG. 2A, the process may be initiated with a response to a request to swap images 210. Once a response to the request to swap images is received the mode is then selected, block 220. If manual mode 222 is selected, the process proceeds as discussed above with a user manually adjusting the image to obtain initial alignment.

More specifically, with regard to manual mode 222, an adjustment is made of the slices associated with the top image, block 230. This may require a vertical image adjustment 232 and a horizontal image adjustment 238. Once these adjustments are made, the images are aligned and joined 244 as is discussed in further detail below.

If the manual mode 222 is not selected, the process proceeds in automatic mode 224. In automatic mode, after the images showing the best overlapping features are selected into the display, an "Auto Join" feature is then selected, block 250, preferably via software. Using mouse or other control a user may then place a cursor on one of the features in the upper image, block 254. (Although this description is done with respect to upper and lower images, it should be apparent to one skilled in the art the images may be arranged in other orientations, e.g., side-by-side, in lieu of an upper/lower orientation.) In this regard, the feature may be a particular portion of the anatomy, such as a particular vertebrae. A second cursor is placed over the corresponding feature in the lower image, block 260, and the 3D volume data is then joined automatically 244 using the best in-plane and out-of-plane offsets. The offsets are computed using an algorithm that minimizes the square of the normalized intensity differences between the pixel neighborhoods of the two cursor locations. The pixel neighborhoods may be in-plane (2 dimensional) or a volume (3 dimensional). That is, in 3D:

$$\min \sum_{i \in N_i} \sum_{j \in N_j} \sum_{k \in N_k} \left[ \frac{G(i,j,k)}{A_G(i,j,k)} - \frac{H(i,j,k)}{A_H(i,j,k)} \right]^2$$

where
$N_i$ is the pixel neighborhood in the i-direction;
$N_j$ is the pixel neighborhood in the j-direction;
$N_k$ is the pixel neighborhood in the k-direction;
$G(i,j,k)$ is the pixel value at i, j, k for the first or upper data;
$H(i,j,k)$ is the pixel value at i, j, k for the second or lower data;
$A_G(i,j,k)$ is the average intensity of the pixel neighborhood centered at i, j, k for the upper data; and
$A_H(i,j,k)$ is the average intensity of the pixel neighborhood centered at i, j, k for the lower data.

The average intensities, $A_G(i,j,k)$ and $A_H(i,j,k)$ are used to normalize the pixel data so as to mitigate differences in common feature intensity levels between the two data sets. The combination of i, j and k which minimizes the function yields the offset values used to translate the images before joining the pixel data.

As discussed above, the neighborhood is chosen based on distinguishing features in the images. In effect, this results in a determination based on distance. If too big of an area is chosen, the computational complexity increases. Once the control points are chosen, a search is performed to determine similarities of the control point neighborhoods. The pixel intensities are used in the above error function to determine the similarities between the two neighborhoods. The images are then offset from each other and the error function is then recalculated. The change in the error function value provides an indication of whether the offset is converging toward an optimal point. In other words, the offsets that minimize the above error function provide the best overlapping match.

FIG. 2B is a flow diagram illustrating the above process. As shown, the process begins at block 262 with the selection of control points in the first and second images. With the control points selected, the neighborhood size is set around the control points based on pre-defined limits, block 264. Next, the neighborhood offset limits are set in the x, y and z directions according to pre-defined values, block 266. The second image neighborhood is then offset with respect to the first image control point, block 270.

Next, the normalized error function is computed based on overlapping neighborhood pixel intensities, block 274. As discussed above, the normalized error function is computed using the above equation. The newly computed normalized error function is compared to the minimum error function, block 276. If the new error function is less than the minimum error function, the minimum error function is replaced by the new error function, block 280, and the x, y and z offsets are incremented, block 282. If the new error function is not less than the minimum error function, the process proceeds directly to block 282.

The process then determines whether the volume search is completed, block 284. That is, a determination is made of whether a search of the pertinent volume of neighborhood pixel data is searched. If the volume search is incomplete, the process returns to block 270 and repeats. If the volume search is completed, the first and second images are joined or stitched together, block 290. A "C" routine that computes the offsets is provided below as part of the specification.

An example of a user interface and a composite image formed using the present invention is shown in FIGS. 3A and 3B. The left image 302 of FIG. 3A shows upper and lower sagittal spine images from two 3D volume data sets. These two data sets are to be combined into one large composite data set by overlapping them with appropriate x, y and z slice shifts. The vertical line 304 indicates an orthogonal plane cut through the 3D volumes and the resulting orthogonal coronal images 312 are shown on the right. This feature is used to facilitate the marking of the two control points 320, 322 that are used as starting locations for the offset computations. After the "Join" procedure is instantiated using the Join Button 328, the offset computations or shift finding process finds the best combination of x, y and z slice shifts and combines the 3D data volumes into a singular composite 3D volume with those shifts. A slice of the new 3D volume 360 is shown on the left side of FIG. 3B and the coronal cut plane resulting from the orthogonal cut 374 is shown on the 364. The shifts determined by the shift process are shown in the shift control panels 380 on the right side of FIG. 3B. As can also be seen from a comparison of FIGS. 3A and 3B, the upper and lower images are now offset from one another as shown by the boxes 384, 388.

The images shown in FIGS. 3A and 3B are of the spine of a patient and demonstrate the use of the methods described herein in detecting, for example, scoliosis. Methods and systems for performing sciolis are described in commonly assigned U.S. application Ser. No. 12/152,139, the disclosure of which is hereby incorporated herein by reference.

A block diagram of a computer system on which the features of the inventions discussed above may be executed is shown in FIGS. 4 and 5. In accordance with one aspect of the invention, system 100 includes a computer 150 containing a processor 152, memory 154 and other components typically present in general purpose computers.

Memory 154 stores information accessible by processor 152, including instructions 180 that may be executed by the processor 152 and data 182 that may be retrieved, manipulated or stored by the processor. The memory may be of any type capable of storing information accessible by the processor, such as a hard-drive, memory card, ROM, RAM, DVD, CD-ROM, write-capable, read-only memories. The memory 154 may contain machine executable instructions or other software programs that embody the methods discussed above and generally shown in FIGS. 2A and 2B. In addition, the code shown below is preferably stored as machine readable instructions in memory 154.

The processor may comprise any number of well known general purpose processors, such as processors from Intel Corporation or AMD. Alternatively, the processor may be a dedicated controller such as an ASIC.

The instructions 180 may comprise any set of instructions to be executed directly (such as machine code) or indirectly (such as scripts or source code) by the processor. Further, the terms "instructions," "steps" and "programs" may be used interchangeably herein. The instructions may be stored in object code form for direct processing by the processor, or in any other computer language including scripts or collections of independent source code modules that are interpreted on demand or compiled in advance. As shown below, the functions, methods and routines of instructions may comprise source code written in "C".

Data 182 may be retrieved, stored or modified by processor 152 in accordance with the instructions 180. The data may be stored as a collection of data and will typically comprise the MRI image or pixel data discussed above. For instance, although the invention is not limited by any particular data structure, the data may be stored in computer registers, in a database as a table having a plurality of different fields and records, XML documents, or flat files. The data may also be formatted in any computer readable format such as, but not limited to, binary values, ASCII or EBCDIC (Extended Binary-Coded Decimal Interchange Code). Moreover, the data may comprise any information sufficient to identify the relevant information, such as descriptive text, proprietary codes, pointers, references to data stored in other memories (including other network locations) or information which is used by a function to calculate the relevant data.

Figure 5:
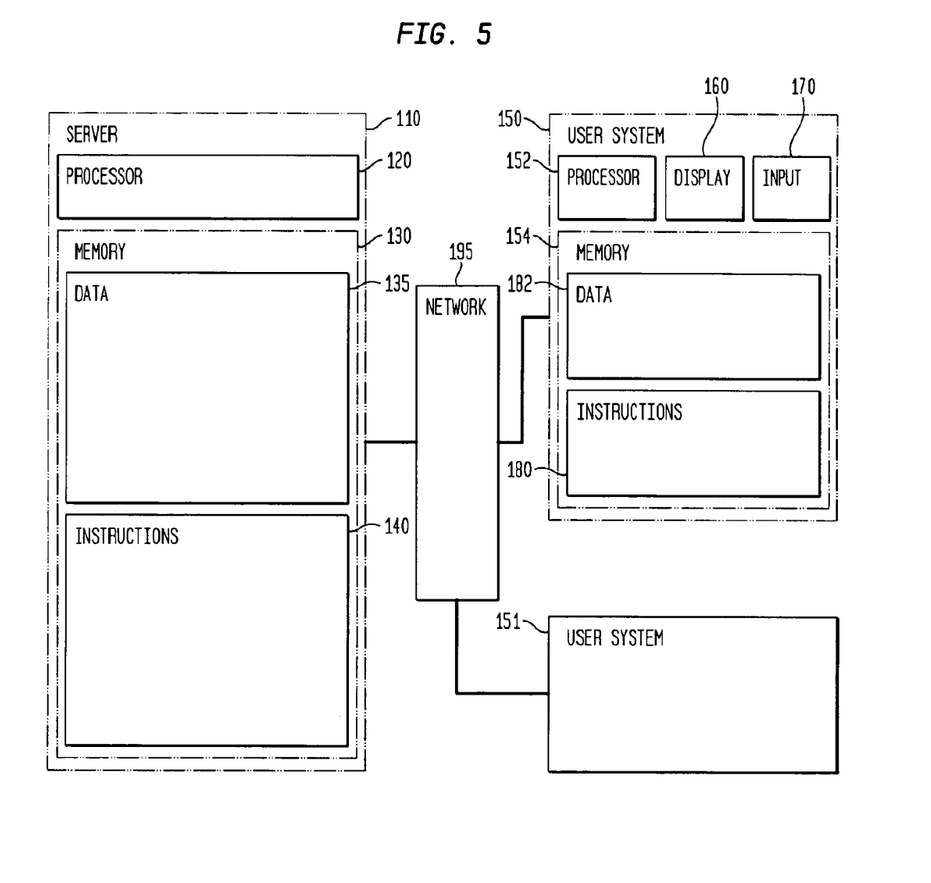
FIG. 5 illustratively depicts a network and equipment that may be used in accordance with an aspect of the present invention.

Although the processor and memory are functionally illustrated in FIG. 5 within the same block, it will be understood by those of ordinary skill in the art that the processor and memory may actually comprise multiple processors and memories that may or may not be stored within the same physical housing. For example, some of the instructions and data may be stored on removable CD-ROM and others within a read-only computer chip. Some or all of the instructions and data may be stored in a location physically remote from, yet still accessible by, the processor. Similarly, the processor may actually comprise a collection of processors which may or may not operate in parallel.

In another aspect, the methods, programs, software or instructions described above may executed via a server 110. This is desirable where many users need to access and view the same data, such as in a hospital or in non-collocated facilities. Server 110 communicates with one or more client computers 150, 151, 153. Each client computer may be configured as discussed above. Each client computer may be a general purpose computer, intended for use by a person, having all the internal components normally found in a personal computer such as a central processing unit (CPU), display 160, CD-ROM, hard-drive, mouse, keyboard, speakers, microphone, modem and/or router (telephone, cable or otherwise) and all of the components used for connecting these elements to one another. Moreover, computers in accordance with the systems and methods described herein may comprise any device capable of processing instructions and transmitting data to and from humans and other computers, including network computers lacking local storage capability, PDA's with modems and Internet-capable wireless phones. In addition to a mouse, keyboard and microphone, other means for inputting information from a human into a computer are also acceptable such as a touch-sensitive screen, voice recognition, etc.

Figure 4:
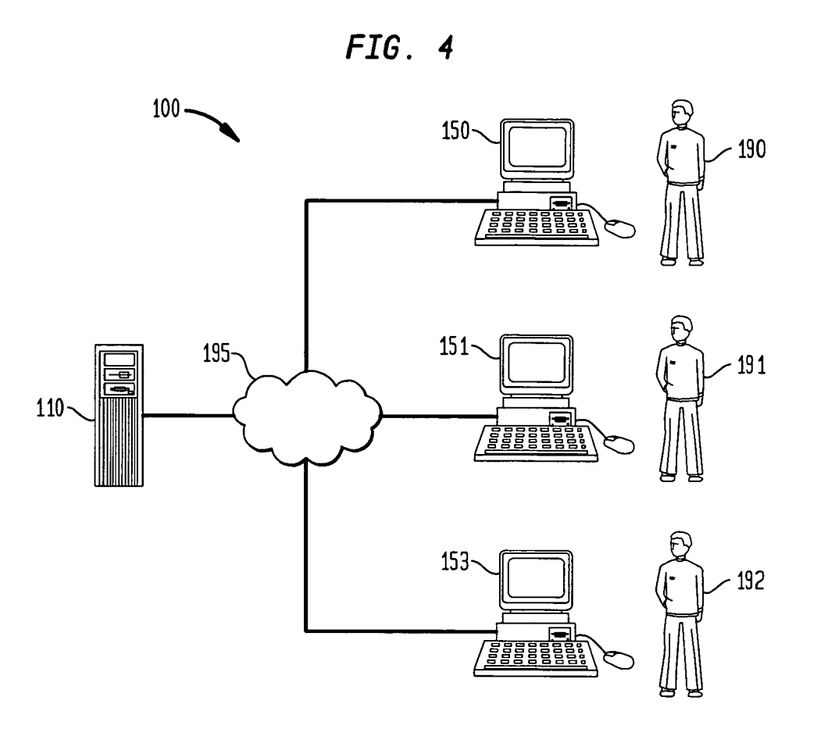
FIG. 4 illustratively depicts a network and equipment that may be used in accordance with an aspect of the present invention.

The server 110 and client computers 150, 151, 153 are capable of direct and indirect communication, such as over a network. Although only a few computers are depicted in FIGS. 4 and 5, it should be appreciated that a typical system can include a large number of connected computers, with each different computer being at a different node of the network. The network, and intervening nodes, may comprise various configurations and protocols including the Internet, intranets, virtual private networks, wide area networks, local networks, private networks using communication protocols proprietary to one or more companies, Ethernet, WiFi and HTTP. Such communication may be facilitated by any device capable of transmitting data to and from other computers, such as modems (e.g., dial-up or cable), networks and wireless interfaces. Server 110 may be a web server. Although certain advantages are obtained when information is transmitted or received as noted above, other aspects of the invention are not limited to any particular manner of transmission of information. For example, in some aspects, the information may be sent via a medium such as a disk, tape, CD-ROM.

The information may also be transmitted over a global or private network, or directly between two computer systems, such as via a dial-up modem. In other aspects, the information may be transmitted in a non-electronic format and manually entered into the system.

It should be understood that the operations discussed above and illustrated, for example, in FIGS. 2 and 3, do not have to be performed in the precise order described above. Rather, various steps may be handled simultaneously and in some instances in reverse order.

Source Code Example

```
void AutoJoin( LPSTUDY lpStudyTop, LPSTUDY lpStudyBot,
        LPIMAGEINFO lpImageRefTop,
        POINT ptTopSeed, POINT ptBotSeed,
        int nTopSliceRef, int nBotSliceRef,
        int * iBot, int * jBot, int * kBot )
{
    int     i, j, k;
    int     iCC, jCC, kCC;
    int     iMax, jMax, kMax;
    int     iOffset, jOffset, kOffset;
    int     iLimitLo, jLimitLo, kLimitLo;
    int     iLimitHi, jLimitHi, kLimitHi;
    int     nLimit;
    int     nHeight, nWidth;
    int     iRange, jRange, kRange;
    double      dTemp;
    double      dSum;
    double      dConvert;
    double      MinCC;
    double      dAvgTop, dAvgBot;
    unsigned short      *usTop, *usBot;
    IMAGE       ImTop, ImBot;
    // make i and j limits 20 mm, k limit 10 mm
    nLimit = RoundDouble( lpImageRefTop->lpImgChunk->pix_per_mm * 20.0 );
    iLimitLo = nLimit;
    iLimitHi = nLimit;
    jLimitLo = nLimit;
    jLimitHi = nLimit;
    kLimitLo = nLimit/2;
    kLimitHi = nLimit/2;
    nHeight = nWidth = lpImageRefTop->lpinfoHeader->biWidth;
    // convert all values to image coordinates
    dConvert = (double)lpImageRefTop->lpInfoHeader->biWidth / lpDisplayImageTop->lpInfoHeader->biWidth;
    ptTopSeed.x = (int)( dConvert * ptTopSeed.x );
    ptTopSeed.y = (int)('dConvert * ptTopSeed.y );
    ptBotSeed.x = (int)( dConvert * ptBotSeed.x );
    ptBotSeed.y = (int)( dConvert * ptBotSeed.y );
    if( ptTopSeed.y - iLimitLo < 0 | | ptBotSeed.y - iLimitLo < 0 )
        iLimitLo = _min( ptTopSeed.y, ptBotSeed.y );
    if( ptTopSeed.x - jLimitLo < 0 | | ptBotSeed.x - jLimitLo < 0 )
        jLimitLo = _min( ptTopSeed.x, ptBotSeed.x );
    if( nTopSliceRef - kLimitLo < lpStudyTop->nScoutOffset | |
 nBotSliceRef - kLimitLo < lpStudyBot->nScoutOffset)
        kLimitLo = _min( nTopSliceRef, nBotSliceRef ) - 1;
    if( ptTopSeed.y + iLimitHi >= nWidth | 51 ptBotSeed.y + iLimitHi >= nWidth )
        iLimitHi = _min( nWidth-ptTopSeed.y, nWidth-ptBotSeed.y ) - 1;
    if( ptTopSeed.x + jLimitHi >= nHeight | | ptBotSeed.x + jLimitHi >= nHeight )
        jLimitHi = min( nHeight-ptTopSeed.x, nHeight-ptBotSeed.x ) - 1;
    if( nTopSliceRef + kLimitHi >= lpStudyTop->NumberImages | |
 nBotSliceRef + kLimitHi >= lpStudyBot->NumberImages)
        kLimitHi = _min( lpStudyTop->NumberImages-nTopSliceRef, lpStudyBot->NumberImages-nBotSliceRef ) -1;
    iRange = iLimitHi+iLimitLo+1;
    jRange = jLimitHi+jLimitLo+1;
    kRange = kLimitHi+kLimitLo+1;
    kCC = jCC = iCC = 0;
    MinCC = 1e20;
    for( kCC = -kLimitLo; kCC <= kLimitHi; kCC++ )
    {
        for( iCC = -iLimitLo; iCC <= iLimitHi; iCC++ )
        {
            for( jCC = -jLimitLo; jCC <= jLimitHi; jCC++ )
            {
                dAvgTop = 0;
                dAvgBot = 0;
                for(k= -kiLimitLo; k<= kLimitHi; k++ )
                {
                    ImTop = lpStudyTop->lpImageInfo[nTopSliceRef+k];
                    usTop = (unsigned short*)ImTop.lp12BitImage;
                    ImBot = lpStudyBot->lpImageInfo[nBotSliceRef+kCC+k];
                    usBot = (unsigned short*)ImBot.lp12BitImage;
                    for( i = -iLimitLo; i <= iLimitHi; i++ )
                    {
                        for( j = -jLimitLo; j <= jLimitHi; j++ )
                        {
                            dAvgTop += (double)usTop[(ptTopSeed.y+i)*nWidth + (ptTopSeed.x+j)];
                            dAvgBot += (double)usBot[(ptBotSeed.y+iCC+i)*nWidth + (ptBotSeed.x+jCC+j)];
                        }
                    }
                }
                dAvgTop /= iRange*jRange*kRange;
                dAvgBot /= iRange*jRange*kRange;
                dSum = 0;
                for( k = -kLimitLo; k <= kLimitHi; k++ )
                {
                    ImTop = lpStudyTop->lpImageInfo[nTopSliceRef+k];
                    usTop = (unsigned short*)ImTop.lp12BitImage;
                    ImBot = lpStudyBot->lpImageInfo[nBotSliceRef+kCC+k];
                    usBot = (unsigned short*)ImBot.lp12BitImage;
                    for( i = -iLimitLo; i <= iLimitHi; i++ )
                    {
                        for( j = -jLimitLo; j <= jLimitHi; j++ )
                        {
                            dTemp = (double)usTop[(ptTopSeed.y+i)*nWidth + (ptTopSeed.x+j)]/dAvgTop - usBot[(ptBotSeed.y+iCC+i)*nWidth + (ptBotSeed.x+jCC+j)]/dAvgBot;
                            dTemp = dTemp*dTemp;
```

-continued

```
         dSum += dTemp;
       }
     }
   }
   if( dSum <= MinCC )
   {
     MinCC = dSum;
     iMax = iCC;
     jMax = jCC;
     kMax = kCC;
   }
     }
   }
 }
 // convert i and j back to screen coordinates
 *iBot = RoundDouble( iMax / dConvert );
 *jBot = RoundDouble( jMax / dConvert );
 *kBot = kMax;
}
```

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. An apparatus, comprising:
a memory containing executable instructions; and
a processor programmed using the instructions to:
  receive pixel data associated with a first magnetic resonance image having
  a first control point;
  receive pixel data associated with a second magnetic resonance image having a second control point, wherein the second image only partially overlaps the first image;
  for each of a plurality of offsets between the first control point and the second control point, compare a first neighborhood of pixels surrounding the first control point and a second neighborhood of pixels surrounding the second control point using the square of the normalized intensity difference between the first neighborhood of pixels and the second neighborhood of pixels;
  combine the images together at one or more places using one of the plurality of offsets based on the comparison between the first neighborhood of pixels and the second neighborhood of pixels, thereby forming a combined image; and
  provide data for displaying the combined image.

2. The apparatus of claim 1, wherein the processor is programmed to compare a first neighborhood of pixels that are in-plane and a second neighborhood of pixels.

3. The apparatus of claim 1, wherein the processor is programmed to compare a first neighborhood of pixels comprising multiple planes of pixels and a second neighborhood of pixels.

4. The apparatus of claim 1, wherein the processor is programmed to compare a first neighborhood of pixels having a rectangular parallelepiped shape and a second neighborhood of pixels.

5. The apparatus of claim 1, wherein the processor is programmed to define each of the first neighborhood of pixels and the second neighborhood of pixels based on a predetermined limit.

6. The apparatus of claim 1, wherein the processor is programmed to define offset values for each of the plurality of offsets based upon predefined values.

7. The apparatus of claim 1, wherein the processor is programmed to define an offset value for each of the plurality of offsets in each of three dimensions.

8. The apparatus of claim 1, wherein the processor is further programmed to provide data for display indicating the offset between the first and second magnetic resonance images used in forming the combined image.

9. The apparatus of claim 1, wherein the processor is further programmed to discard select image data from the first and second image data based on the detected common area.

10. The apparatus of claim 1, wherein in comparing the first neighborhood of pixels and the second neighborhood of pixels, the processor is programmed to search volumetric data associated with the first and second neighborhoods of pixels.

11. The apparatus of claim 1, wherein the processor is further programmed to provide data for displaying at least two views of the combined image with one view being orthogonal to the other.

12. The apparatus of claim 1, wherein the processor combines the images based on in-plane and out-of-plane offsets.

13. The apparatus of claim 1, wherein, for each of the plurality of offsets, the processor is programmed to determine a degree of similarity between the first neighborhood of pixels and the second neighborhood of pixels, and combine the images using the offset for which the corresponding degree of similarity is minimized, wherein a lower degree of similarity indicates a greater similarity between the compared neighborhoods of pixels.

* * * * *